United States Patent
Massaro et al.

(10) Patent No.: US 7,246,551 B2
(45) Date of Patent: Jul. 24, 2007

(54) LIQUID HANDLING DEVICE WITH SURFACE FEATURES AT A SEAL

(75) Inventors: Peter Massaro, Burlington, CT (US); Michael Paschetto, Hampden, MA (US)

(73) Assignee: Protedyne Corporation, Windsor, CT (US)

( * ) Notice: Subject to any disclaimer, the term of this patent is extended or adjusted under 35 U.S.C. 154(b) by 328 days.

(21) Appl. No.: 10/887,706

(22) Filed: Jul. 9, 2004

(65) Prior Publication Data

US 2006/0008370 A1  Jan. 12, 2006

(51) Int. Cl.
*F01B 31/10* (2006.01)
*A61M 5/31* (2006.01)

(52) U.S. Cl. ............................ 92/158; 92/153; 604/230

(58) Field of Classification Search .................. 92/153, 92/158, 159; 604/230
See application file for complete search history.

(56) References Cited

U.S. PATENT DOCUMENTS

| | | | |
|---|---|---|---|
| 1,028,426 A | 6/1912 | Brammer | |
| 1,771,219 A | 7/1930 | Hein | |
| 2,618,264 A * | 11/1952 | Bloxsom | 604/230 |
| 2,771,880 A | 11/1956 | Gotthart | |
| 4,030,498 A * | 6/1977 | Tompkins | 604/152 |
| 4,067,401 A * | 1/1978 | Schnell | 92/153 |
| 4,435,989 A | 3/1984 | Meyer et al. | |
| 4,442,722 A | 4/1984 | Meyer | |
| 5,038,673 A * | 8/1991 | Schulze | 92/71 |
| 5,218,875 A | 6/1993 | Volpe et al. | |
| 5,353,691 A | 10/1994 | Haber | |
| 5,525,302 A | 6/1996 | Astle | |
| 5,577,896 A * | 11/1996 | Harada | 417/259 |
| 6,093,175 A * | 7/2000 | Gyure et al. | 604/230 |
| 6,123,905 A | 9/2000 | Torti et al. | |
| 6,258,324 B1 | 6/2001 | Yiu | |
| 6,331,174 B1 * | 12/2001 | Reinhard et al. | 604/232 |
| 6,544,479 B1 | 4/2003 | Astle | |
| 6,601,433 B2 | 8/2003 | Kriz et al. | |
| 6,627,160 B2 | 9/2003 | Wanner | |
| 2001/0039400 A1 | 11/2001 | Lubrecht | |

FOREIGN PATENT DOCUMENTS

EP  0962229 A  12/1999

OTHER PUBLICATIONS

International Search Report PCT/US2005/024281 dated Dec. 2, 2005.

\* cited by examiner

*Primary Examiner*—Michael Leslie
(74) *Attorney, Agent, or Firm*—Wolf, Greenfield & Sacks, P.C.

(57) ABSTRACT

A sample handling tool includes a body having at least one plunger associated with a channel and arranged for axial movement within the channel. A seal is provided in the channel and sealingly engaged with a contact surface. The contact surface may include a surface feature, such that when contact surface moves, the seal and surface feature come into at least partial contact with one another. The seal may include an elastomeric member, such as an O-ring or X-ring, and the contact surface may be formed from any suitable material, including ceramic. The surface feature may take on a variety of forms including any suitable texture, surface porosity or include one or more grooves, holes, recesses, indentations, bumps, protrusions, etc., or a combination thereof.

31 Claims, 5 Drawing Sheets

LIQUID HANDLING DEVICE WITH SURFACE FEATURES AT A SEAL

FIELD OF INVENTION

This invention relates to sample handling tools, such as pipetting devices. More particularly, this invention relates to plunger-operated pipettes for aspirating and dispensing samples of material.

BACKGROUND OF INVENTION

Sample handing tools having a plurality of pipetting devices are widely used, for example in proteomic and genomic research and in laboratory and clinical procedures which require a predetermined amount of material to be taken from one work area and dispensed on another work area. These devices are used to move material samples both to and from a variety of different types of work areas, such as microtiter trays, gels having separated DNA fragments, and other material holding devices. Some such tools may have a plurality of pipetting devices arranged in an array that corresponds to wells in a microtiter tray, such as the commonly-known 96-well or 384-well plate. This arrangement may allow material to be simultaneously deposited in, and removed from, wells in the microtiter tray, thus increasing the speed at which a plurality of samples in a microtiter tray are processed.

The pipetting devices in the tool typically include a plunger or piston that moves within a channel. The plunger may be actuated in one direction to draw fluid into the channel, e.g., to cause aspiration of a sample at a corresponding needle or pipette tip, and in the opposite direction to discharge fluid from the channel, e.g., to dispense a sample. A seal is typically provided between the plunger and channel to create a pressure differential as the plunger is moved in the channel. Commonly, the plunger is made with a highly polished or otherwise smooth surface, and forms a seal with an O-ring or other member mounted on the channel. The integrity of the seal is important to being able to draw and discharge material into and from the pipette. Thus, a longer useful life and reliability for the seal is desirable.

SUMMARY OF INVENTION

In one aspect of the invention, the plunger and/or the channel are arranged to improve the service life and/or volume accuracy of the pipetting device. In one illustrative embodiment, the plunger and/or the channel may have a sealing surface that includes a surface feature, such as a groove, pit, protuberance, cavity, etc., that forms a non-smooth surface at a seal between the plunger and the channel. For example, the plunger may have a surface feature in the form of one or more grooves, and the grooved portion of the plunger may sealingly engage with a resilient seal member mounted to the channel as the plunger moves in the channel to aspirate and/or dispense a sample. The inventor has unexpectedly found that providing a surface feature, at least in part, in place of the typically smooth contact surface found in prior devices improves performance of the device. Improved performance characteristics that have been unexpectedly found include a longer wear life, reduced maintenance and improved volume control.

In one illustrative embodiment in accordance with the invention, a liquid handling device includes a body with at least one channel, the channel having an end for receiving and expelling fluid. A plunger is constructed and arranged for axial movement within the channel, and a contact surface is provided including a surface feature that forms a non-smooth surface. A seal is provided in the channel that sealingly engages a portion of the plunger with a portion of the body, and at least a portion of the contact surface including the surface feature is located at the seal. Movement of the plunger in the channel causes movement of the body relative to the plunger at the seal and causes fluid flow at the end of the channel.

In one aspect of the invention, the surface feature may include one or more grooves, holes, recesses, bumps, protrusions, cavities, pits, etc, and may be provided at a portion of the contact surface that is sealingly engaged at a seal, e.g., formed by contact of an elastomeric member with the contact surface.

In another embodiment of the invention, a liquid handling apparatus includes a body with at least one channel and a needle in communication with the channel. The apparatus also includes a piston constructed and arranged for axial movement within the channel. An engagement surface is provided with a surface means for lubricating and a seal is provided in the channel that sealingly contacts the engagement surface. Movement of the piston causes relative movement of the engagement surface and the seal and causes fluid flow in the needle.

In another aspect of the invention, a liquid handling apparatus includes a body with at least one channel and a needle in communication with the channel, the needle having an open end for receiving and expelling fluid. The apparatus also includes a plunger constructed and arranged for axial movement within the channel. The plunger has a contact surface with at least one groove provided on the contact surface. An X-ring is mounted in the channel and sealingly engages with the contact surface of the plunger. Movement of the plunger in the channel causes relative movement of the contact surface and the X-ring and causes fluid flow at the open end of the needle.

These and other aspects of the invention will be apparent and/or obvious from the following description of illustrative embodiments and the appended claims.

BRIEF DESCRIPTION OF DRAWINGS

Aspects of the invention will be more clearly appreciated from the following detailed description, when taken in conjunction with the accompanying drawings, wherein like numbers are used for like features, in which.

DETAILED DESCRIPTION

Various aspects of the invention are described below with reference to illustrative embodiments. However, it should be understood that the invention is not limited to those embodiments described below, but instead may be used in any suitable system or arrangement.

In one aspect of the invention, a sample handling tool includes a body with a plunger arranged for axial movement in a channel in the body. A seal provided in the channel is sealingly engaged with a contact surface. In one embodiment, the seal is formed by a seal member provided on the channel that engages with a contact surface provided on the plunger, although the locations of the seal member and contact surface may be reversed. When the plunger is axially moved in the channel, e.g., to aspirate or dispense a sample, the seal member and contact surface move relative to each other, preferably maintaining sealing engagement with each other during movement.

In accordance with one aspect of the invention, the contact surface has a surface feature which may include a texture, porosity, grooves, holes, recesses, indentations, protrusions, bumps, cavities, and/or pits, which is in contrast to conventional liquid handling devices that include smooth contact surfaces at the engagement with a seal. Lubricant may be partially engaged in the surface feature to assist in providing the sealing engagement between the contact surface and the seal, and/or lubricating other moving surfaces and may result in reduced wear of the components. That is, lubricant at the surface feature may be retained at the surface feature (rather than being wiped away by a seal member as in conventional smooth surfaced devices) and aid in lubricating the moving parts. Also, the surface feature may reduce the sticking and/or moving friction between parts and allow for more controllable plunger movement and therefore more accurate volume control.

The contact surface that has the surface feature may be made of ceramic, plastic, glass, metal or combinations of any suitable material. The seal may be formed by any suitable sealing device, such as an elastomeric seal member, e.g., an O-ring, X-ring or any other suitable device and may be mounted to either the body or the plunger. The seal may also be formed by a close fit of portions of the plunger and body, suitable bearings or other suitable arrangements, and not necessarily by a resilient device or other seal member.

In yet another aspect of the invention, the contact surface may engage a seal member, e.g., an X-ring, at at least two contact points during relative motion of the contact surface and the seal. This arrangement may assist in providing the sealing engagement or lubrication between the seal and contact surface, furthering the improved performance characteristics, such as a longer wear life for the components of the device, reduced maintenance and closer volume control.

Figure 1:
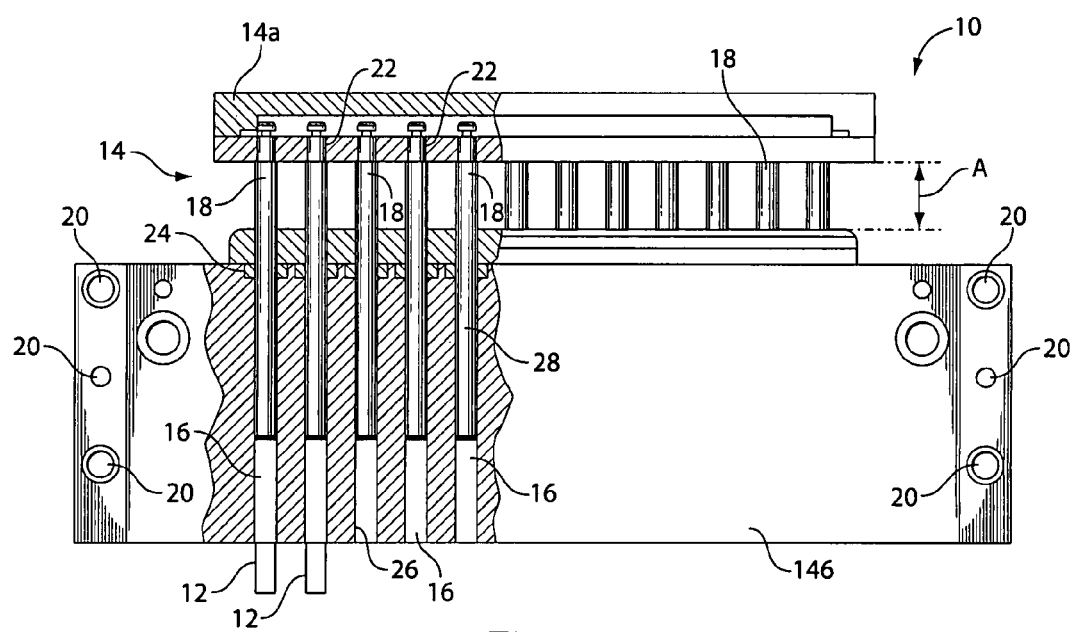
FIG. 1 is a schematic diagram of a sample handling apparatus according to the invention.

An illustrative embodiment of a sample handling apparatus 10 that incorporates various aspects of the invention is shown in FIG. 1. The apparatus 10 includes needles 12 to take-up and/or dispense material on one or more work areas, such as microtiter trays, gels containing separated DNA fragments or other biologic materials, etc. The needles 12 may carry a replaceable pipette tip (not shown) or other suitable devices to handle materials, or may be arranged to handle materials directly as is known in the art. As described herein, the apparatus 10 is used for aspirating and dispensing fluids. However, it will be appreciated that aspects of the invention are not so limited and may be used to handle any material, whether or not a fluid. As used herein, the term "fluid" refers to gases and/or liquids and/or liquids including solid materials.

The apparatus 10 may be moved, either manually or robotically as will be understood in the art, to position one or more needles 12 with respect to a microtiter tray or other sample holding device. It will be appreciated that any suitable number of needles 12 may be arranged in any suitable pattern, such as a pattern that allows the needles to interact with standard 96-well, 384-well or other size configuration microtiter trays or other sample holders. Thus, the illustrative embodiment is used for simplicity and ease of reference, but should in no way be interpreted as limiting aspects of the invention. As will also be understood, one or more plungers 18 may be moved to actuate one or more needles 12 to aspirate fluid from, or dispense fluid in, wells in the sample holding device. Those of skill in the art will understand that the needles 12 may be actuated to perform other material handling operations, such as colony or plaque picking. The purposes and methods for such material handling are well known to those in the art and not described in detail herein.

In this illustrative embodiment, the apparatus 10 includes a body or block 14 with an upper portion or lift plate 14a and a lower portion 14b. The body 14 may be formed in any suitable way, e.g., the upper and/or lower portions 14a and 14b may be made of multiple layers of plastic material that have grooves, channels or are otherwise formed and later assembled to create the desired channels, etc. in the tool body. These layers may be joined together, e.g., by heating and pressing them together, to form a unitary block. Apertures 20 may be used to fasten the body 14 to a framework or other supporting structure, although in robotic applications the body may include a connector that mates with a corresponding connector on the robotic device and provides electric power, control signals, a fluid supply, etc to the tool. Any suitable drive mechanism (not shown, e.g., including guideways for guiding the movement of the upper portion 14a relative to the lower portion 14b, a linear motor that provides the motive force to move the upper portion 14a, and a linear encoder that provides position feedback of the upper portion 14a relative to the lower portion 14b), may be provided to move the upper portion 14a of the body 14 relative to the lower portion 14b, e.g., in a direction shown by the arrow A. Such movement may cause plungers or pistons 18 carried at a top end 22 by the upper portion 14a to move in a range of motion relative to the lower portion 14b within channels 16 and create a pressure differential to cause a corresponding needle 12 to aspirate/dispense a sample. A seal 24 is formed in each of the channels 16 so that movement of a plunger 18 may create a suitable pressure differential to actuate a needle 12. It should be appreciated that the apparatus 10 need not necessarily be constructed precisely as shown in this illustrative embodiment, but may actuate the needles 12 using other mechanisms.

Figure 2:
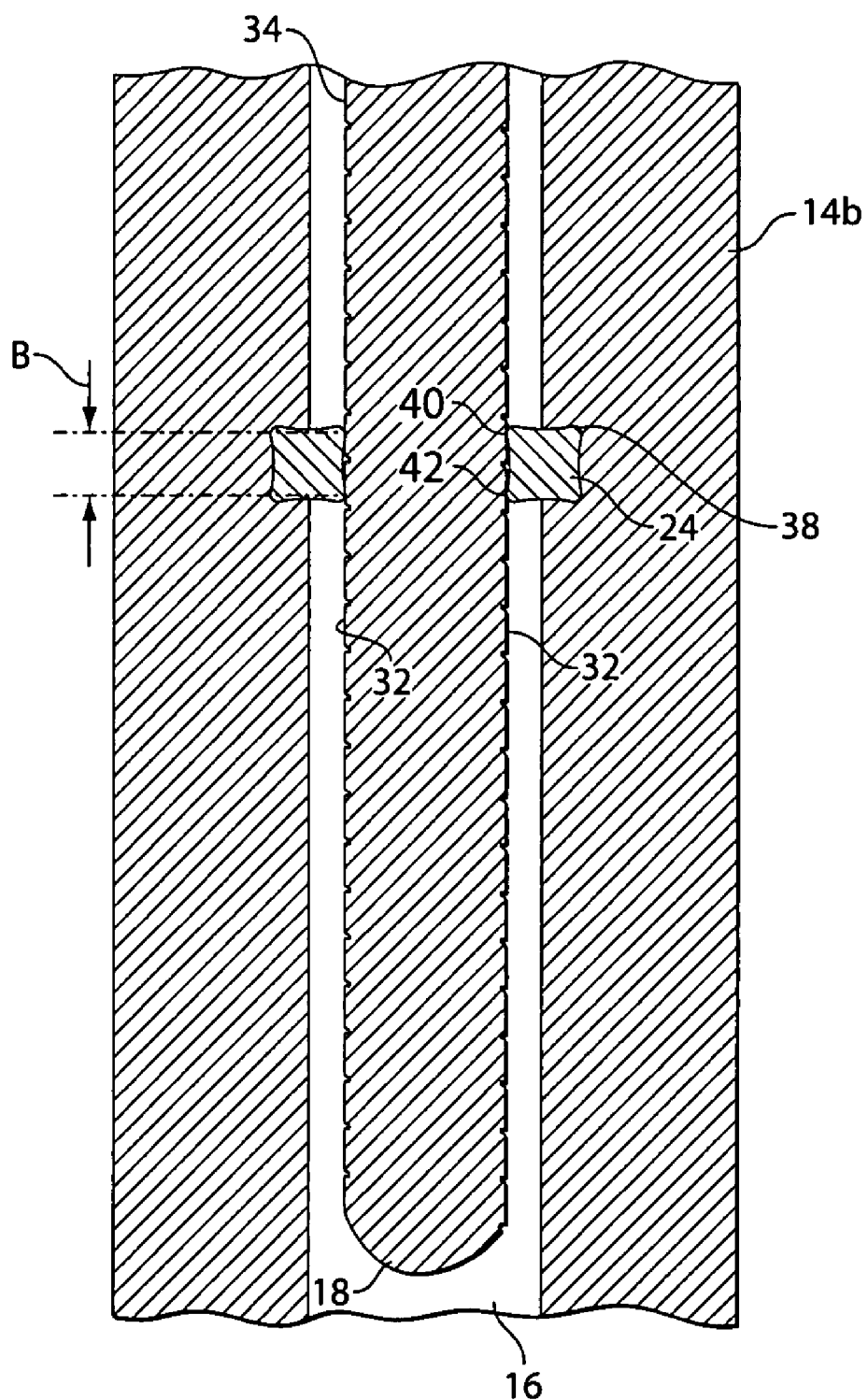
FIG. 2 is a cross-sectional view of a plunger, seal and channel according to one aspect of the invention.
Figure 6:
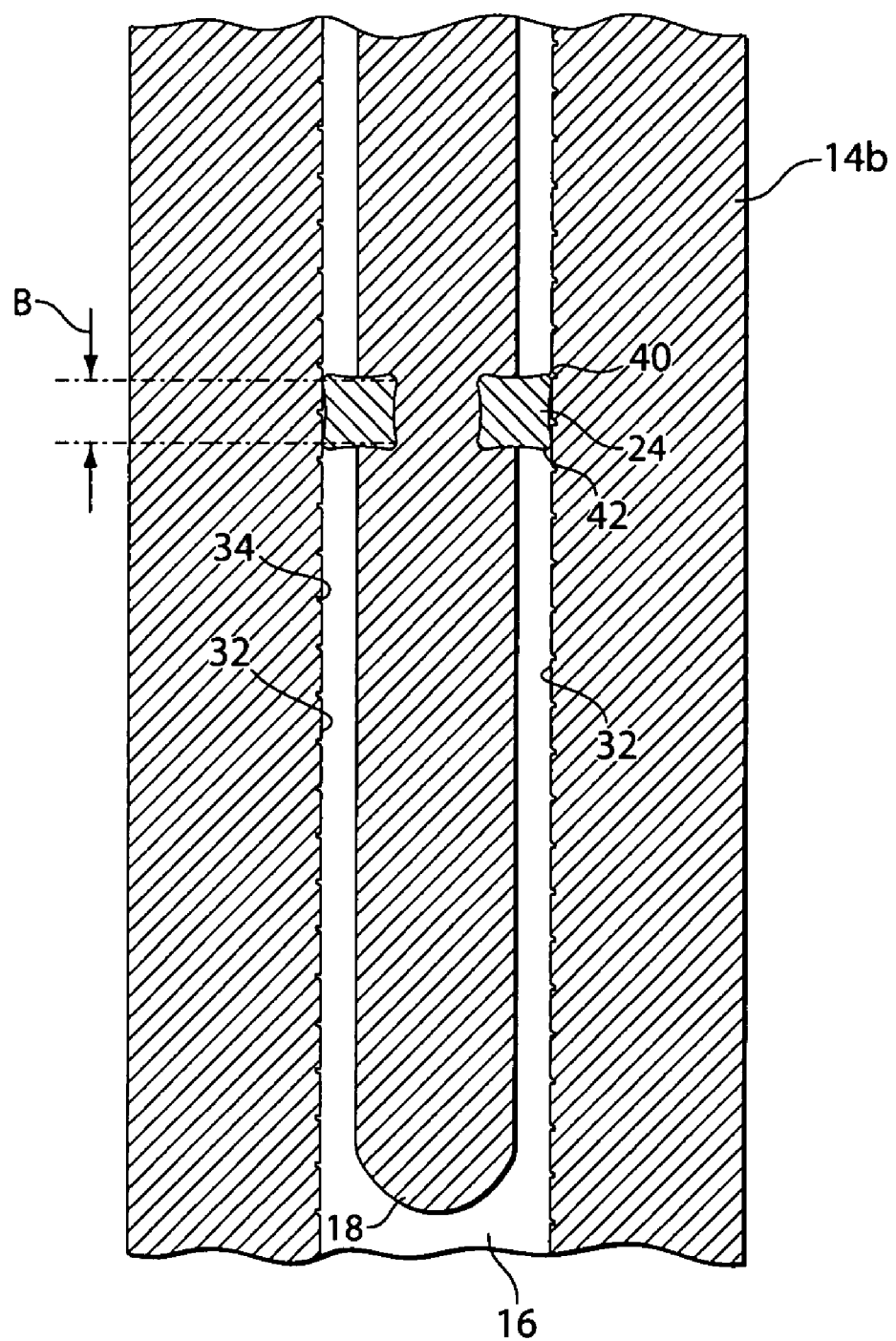
FIG. 6 is a cross-sectional view of a plunger seal and channel according to another aspect of the invention.

FIG. 2 shows a cross-sectional view of a plunger 18 arranged in the body 14 in accordance with one aspect of the invention. A seal is formed between the plunger 18 and the body 14 so that relative movement of the plunger 18 and body 14 causes a pressure change in the channel 16. The seal may be formed by a close fit of the plunger 18 and channel 16 and/or by separate sealing devices. In this embodiment, one or more seal members 24, such as an elastomeric member, is mounted in the channel 16 and contacts an engagement or contact surface 32 of a corresponding plunger 18 (in this case the exterior surface of the plunger 18) and resist fluid flow from within the channel 16 past the plunger 18. As shown in FIG. 6, the seal member 24 may alternately be mounted to the plunger 18 for movement with the plunger 18 relative to the body 14. The contact surface 32 (whether on the plunger 18, the channel 16 or elsewhere) may include surface features 34 that contact the seal member 24 in at least part of the range of motion of the plunger 18. The surface feature 34 presents a relatively rough or non-smooth surface at the seal in contrast to prior arrangements. Surprisingly, the surface feature 34 provides a suitable sealing surface for pipetting applications, yet has been found to reduce wear and increase service life in some applications.

Figure 3:
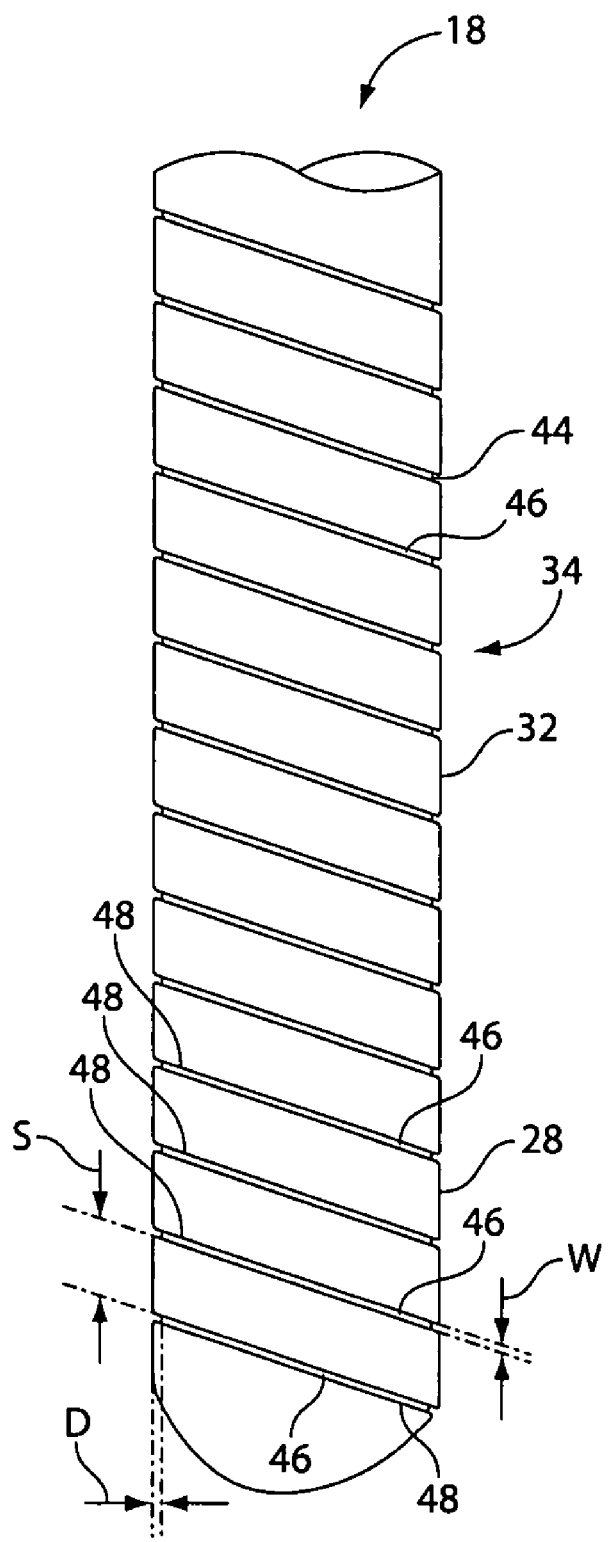
FIG. 3 is a side plan view of the plunger of FIG. 2.
Figure 4:
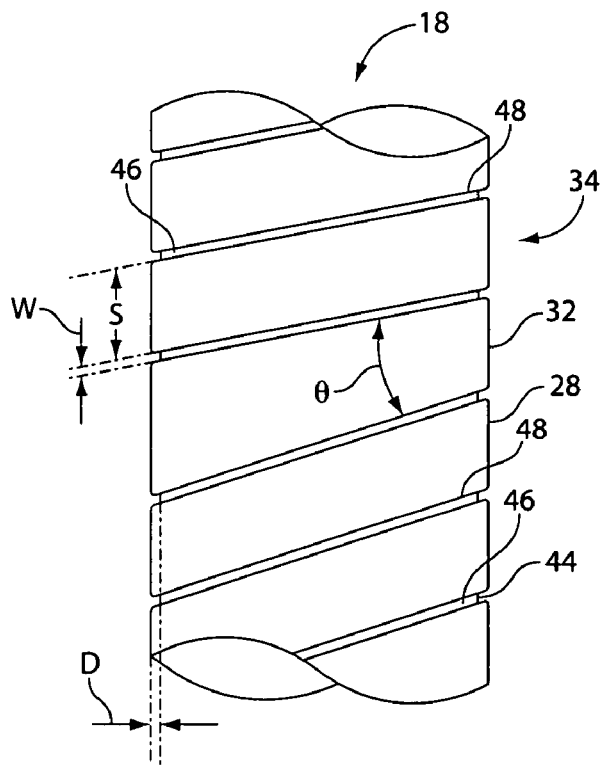
FIG. 4 is a detailed view of the plunger of FIG. 3.

FIG. 3 shows an illustrative embodiment of one type of surface feature 34 that includes a recess 44 formed as a spiral-shaped groove 46. The groove 46 may have any suitable width W and depth D, such as 1-2 millimeters or less. Portions 48 of the groove 46 may have a spacing S between one another, with the spacing S being any suitable value. The arrangement of the groove 46 may allow lubricant to fill the groove 46 and allow a sealing engagement to remain between the contact surface 32 and the seal member 24. As illustrated, the groove 46 is formed as a continuous spiral or helix. However, it will be appreciated that one or more grooves 46 may be provided in any suitable way, e.g., grooves 46 may cross-over each other at any desired angle and may have the same or different widths W, depths D and spacing S. For example, as illustrated in FIG. 4, the angle θ of the portions 48 of the groove 46 relative to one another may vary in any suitable way.

Although FIG. 3 shows one type of surface feature 34 for a particular embodiment, a surface feature 34 in accordance with the invention may include any suitable texture, recesses, indentations, protrusions, cavities, pits, grooves, pores or other features, or a combination thereof, provided on at least a part of the contact surface 32. The surface features 34 may be uniform and/or regularly placed on the contact surface 32. Alternately, the surface features 34 may be irregular and/or randomly placed on the contact surface 32.

Figure 5:
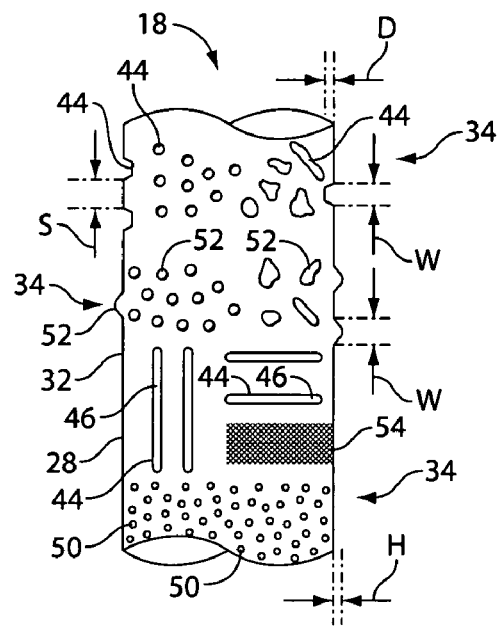
FIG. 5 is a detailed view of alternative surface features according to the invention.

FIG. 5 illustrates other surface features 34 that may be used in aspects of the invention. For example, a part of the contact surface 32 may be porous and include pores 50 open on the surface 28. In one aspect of the invention, the pores may assist in providing lubricant from inside the plunger, e.g., through one or more channels inside the plunger. Alternately, the surface features 34 may include various recesses 44 and/or protrusions 52, such as that illustrated in FIG. 5. It will be appreciated that these recesses 44 and protrusions 52 may have any suitable shape and/or size and/or orientation, etc, and may have any suitable depth D, width W, or height H. These may be regularly or randomly placed about the contact surface 32. In another embodiment, recesses, protrusions and/or other features may form a texture 54 on at least a part of the contact surface 32. The texture 54 may include a variety of different surface treatments, including roughening or etching a part of the contact surface 32.

In one aspect of the invention, a seal member 24 has two contact points 40 and 42 that are displaced axially and individually engage the contact surface 32 at different axial locations, as shown in FIG. 2. The contact points 40 and 42 may be displaced from each other by any suitable distance B. In one aspect of the invention, the seal member 24 includes an X-ring, as illustrated, which includes two points of contact that engage the contact surface 32. In some embodiments, this arrangement has been found to be particularly effective when used with a contact surface 32 having a surface feature 34, e.g., by providing a fluid-tight seal and facilitating lubrication. It will be appreciated that the seal member 24 may be any suitable seal, including one or more O-rings. The seal member 24 may be mounted in any suitable manner as is known in the art, including fitting and adhesively bonding the seal member 24 within a mounting recess 38 formed in the channel 16.

Although the seal in the illustrated embodiments is formed by a resilient seal member, a seal may be formed in other ways, such as by a close fit of the plunger 18 and channel 16, suitable bearings, or other devices. In this embodiment, the seal member 24 remains stationary relative to the channel 16, but in alternate embodiments may move with the plunger 18 and contact an engagement surface on the channel wall. In another embodiment, the contact surface 32 may be formed on an inner surface of the plunger 18, e.g., if the plunger 18 has a tube-like shape, and the seal may be formed inside of the plunger 18, e.g., by a seal member that is carried on a stem inside the tube-like plunger 18.

Lubricant placed on the plunger 16 may at least partially engage the surface feature 34 and may assist in providing the sealing engagement at the seal. In one embodiment, lubricant carried in the surface features 34 may self-lubricate the seal by using lubricant caught in the surface feature 34. This action may reduce wear of the various parts of the apparatus. The lubricant may be any suitable material, e.g., oil, grease or the like. Thus, the surface feature 34 may function as a surface means for lubricating moving parts, e.g., at the seal. This function of lubricating may be performed by retaining lubricant in the surface feature 34, e.g., in grooves or between protrusions, etc., or by providing lubricant to the surface feature 34, e.g., by providing a lubricating oil under pressure within the plunger to pores on the plunger contact surface 32.

Any of the surface features 34 described above may be used alone or in combination with one another in random and/or regular patterns on at least a part of the contact surface 32. The surface features 34 may be rounded, curved or have angular edges. The size and/or shape of the surface features 34 may be the same or different from each other. Moreover, although particular surface features 34 have been illustrated and described, the surface feature 34 is not intended to be limited to those embodiments described herein. It will be appreciated that one of skill in the art may derive numerous other suitable surface features 34.

The pores 50, recesses 52, protrusions 54 and grooves 46, etc. of a surface feature 34 may be formed in any suitable manner of any suitable material. In a preferred embodiment, the surface feature 34 or contact surface 32 is at least partially formed of ceramic. The surface feature 34 may be formed by any suitable process, including machining, molding, abrasion and etching. The channel 16 or plunger 18, which may include the contact surface 32 having the surface feature 34, may be formed first and the surface feature 34 may then be applied to the contact surface 32. For example, the plunger 18 may be cast or molded first and then the surface feature 34 may be machined into the contact surface 32, or the plunger 18 and the surface feature 34 may be formed separately and then assembled together. Alternatively, the surface feature 34 and the channel 16 or plunger 18 may be formed simultaneously, such as by molding.

The surface features 34 may not always be in contact with the seal throughout the entire range of motion of the plunger 18. Instead, the seal may be formed at relatively smooth parts of the contact surface 32 in one portion of the range of motion, and then be formed at the surface feature 34 portion of the contact surface 32 in another portion of the range of motion.

The plunger 18 is illustrated as being solid, however, the plunger 18 may be hollow or include a fluid pathway within the plunger as is known in the art. The plungers 18 and upper and lower portions 14a and 14b may be made of any suitable material(s), such as ceramic, plastic, glass or suitable metal, and the channels and other features may be formed in any suitable way using any suitable process.

While the invention has been described with reference to various illustrative embodiments, the invention is not limited to the embodiments described. Thus, it is evident that many alternatives, modifications, and variations of the embodiments described will be apparent to those skilled in the art. Accordingly, embodiments of the invention as set forth herein are intended to be illustrative, not limiting. Various changes may be made without departing from the invention.

What is claimed is:

1. A liquid handling device comprising:
    a body with at least one channel, the channel having an end for receiving and expelling fluid;
    a needle in fluid communication with the end of the channel to aspirate and/or dispense a fluid sample on a work area;
    a plunger constructed and arranged for axial movement within the channel;
    a contact surface including a surface feature that forms a non-smooth surface; and
    a seal provided in the channel that sealingly engages a portion of the plunger with a portion of the body, the seal including a seal member mounted on the body, and at least a portion of the contact surface including the surface feature being located at the seal;
    wherein the plunger includes the contact surface for sealing engagement with the seal member, and movement of the plunger in the channel causes movement of the body relative to the plunger at the seal and causes fluid flow at the end of the channel that is effective to aspirate and/or dispense the fluid sample on the work area via the needle.

2. The device of claim 1, wherein lubricant is at least partially engaged in the surface feature on the contact surface to assist in providing the sealing engagement at the seal.

3. The device of claim 1, wherein at least a portion of the contact surface moves with the plunger.

4. The device of claim 3, wherein at least a portion of the surface feature engages the seal within a range of motion of the plunger.

5. The device of claim 1, wherein the surface feature includes at least one recess.

6. The device of claim 5 wherein the recess includes at least one groove.

7. The device of claim 1, wherein the surface feature includes at least one protrusion.

8. The device of claim 1, wherein the surface feature includes a porous surface.

9. The device of claim 1, wherein the contact surface is formed from ceramic.

10. The device of claim 1, further comprising:
    the channel being one of a plurality of channels, each of the channels having an open end for receiving and expelling fluid;
    the plunger being one of a plurality of plungers, each of the plungers associated with a corresponding channel;
    the contact surface being one of a plurality of contact surfaces, each contact surface including a surface feature; and
    the seal being one of a plurality of seals, each of the seals provided in a corresponding channel and sealingly engaging a portion of a corresponding plunger with a portion of the body.

11. A liquid handling device comprising:
    a body with at least one channel, the channel having an end for receiving and expelling fluid;
    a needle in fluid communication with the end of the channel to aspirate and/or dispense a fluid sample on a work area;
    a plunger constructed and arranged for axial movement within the channel;
    a contact surface including a surface feature that forms a non-smooth surface; and
    a seal provided in the channel that sealingly engages a portion of the plunger with a portion of the body, the seal including a seal member mounted on the plunger, and at least a portion of the contact surface including the surface feature being located at the seal;
    wherein the channel includes the contact surface for sealing engagement with the seal member, and movement of the plunger in the channel causes movement of the body relative to the plunger at the seal and causes fluid flow at the end of the channel that is effective to aspirate and/or dispense the fluid sample on the work area via the needle.

12. A liquid handling device comprising:
    a body with at least one channel, the channel having an end for receiving and expelling fluid;
    a needle in fluid communication with the end of the channel to aspirate and/or dispense a fluid sample on a work area;
    a plunger constructed and arranged for axial movement within the channel;
    a contact surface including a surface feature that forms a non-smooth surface; and
    a seal provided in the channel that sealingly engages a portion of the plunger with a portion of the body, the seal including a seal member with at least two contact points constructed and arranged for sealing engagement at displaced locations on the contact surface, and at least a portion of the contact surface including the surface feature being located at the seal;
    wherein movement of the plunger in the channel causes movement of the body relative to the plunger at the seal and causes fluid flow at the end of the channel that is effective to aspirate and/or dispense the fluid sample on the work area via the needle.

13. The device of claim 12, wherein the seal member includes an X-ring.

14. A liquid handling apparatus comprising:
    a body with at least one channel;
    a needle in communication with the channel;
    a piston constructed and arranged for axial movement within the channel;
    an engagement surface including a surface means for retaining lubricant; and
    a seal provided in the channel between the piston and the body, the seal including a seal member mounted on the body, and sealingly engaging the piston and the channel at a portion of the engagement surface, wherein the piston includes the engagement surface for sealing contact with the seal member, and movement of the piston in the channel causes fluid flow in the needle.

15. The apparatus of claim 14, wherein lubricant is at least partially engaged in the surface means on the engagement surface to assist in providing the sealing contact of the engagement surface at the seal.

16. The apparatus of claim 14, wherein the engagement surface moves with the piston.

17. The apparatus of claim 16, wherein at least a portion of the surface means contacts the seal within a range of motion of the piston.

18. The apparatus of claim 14, wherein the surface means includes at least one recess.

19. The apparatus of claim 18, wherein the recess includes at least one groove.

20. The apparatus of claim 14, wherein the surface means includes at least one protrusion.

21. The apparatus of claim 14, wherein the surface means includes a porous surface.

22. The apparatus of claim 14, wherein the engagement surface is formed from ceramic.

23. The apparatus of claim 14, wherein:
the seal member includes at least two contact points constructed and arranged for sealing engagement with the contact surface.

24. The apparatus of claim 23, wherein the seal member includes an X-ring.

25. The apparatus of claim 14, further comprising:
the channel being one of a plurality of channels;
the needle being one of a plurality of needles, each of the needles in communication with a corresponding channel;
the piston being one of a plurality of pistons, each of the pistons associated with a corresponding channel;
the engagement surface being one of a plurality of engagement surfaces, each engagement surface including a surface means; and
the seal being one of a plurality of seals, each of the seals provided in a corresponding channel and sealingly engaging a portion of a corresponding piston with a portion of the body.

26. A liquid handling apparatus, comprising:
a body with at least one channel;
a needle in communication with the channel, the needle having an open end for receiving and expelling fluid;
a plunger constructed and arranged for axial movement within the channel, the plunger having a contact surface;
at least one groove provided on the contact surface; and
an X-ring mounted to the channel and sealingly engaged with the contact surface of the plunger,
wherein movement of the plunger in the channel causes fluid flow at the open end of the needle.

27. The apparatus of claim 26, wherein the plunger is formed of a ceramic.

28. The apparatus of claim 26, wherein lubricant on the plunger is at least partially engaged in the at least one groove to assist in providing the sealing engagement between the contact surface and the X-ring.

29. The apparatus of claim 26, wherein the contact surface moves relative to the X-ring within a range of motion of the plunger.

30. The apparatus of claim 26, wherein at least a portion of the groove contacts the X-ring during the range of motion of the plunger.

31. The apparatus of claim 26, further comprising:
the channel being one of a plurality of channels;
the needle being one of a plurality of needles, each of the needles in communication with a corresponding channel;
the plunger being one of a plurality of plungers, each of the plungers associated with a corresponding channel;
the contact surface being one of a plurality of contact surfaces, each contact surface provided on a plunger and including at least one groove; and
the X-ring being one of a plurality of X-rings, each of the X-rings mounted to a corresponding channel and sealingly engaged with a corresponding contact surface.

* * * * *